US009358357B2

(12) United States Patent
Jatana et al.

(10) Patent No.: US 9,358,357 B2
(45) Date of Patent: Jun. 7, 2016

(54) TRACHEOSTOMY TUBE COLLAR AND METHOD

(71) Applicant: Research Institute at Nationwide Children's Hospital, Columbus, OH (US)

(72) Inventors: Kris R. Jatana, Columbus, OH (US); Charles A. Elmaraghy, Dublin, OH (US)

(73) Assignee: Research Institute at Nationwide Childrens' Hospital, Columbus, OH (US)

( * ) Notice: Subject to any disclaimer, the term of this patent is extended or adjusted under 35 U.S.C. 154(b) by 379 days.

(21) Appl. No.: 13/788,460

(22) Filed: Mar. 7, 2013

(65) Prior Publication Data

US 2013/0233322 A1  Sep. 12, 2013

Related U.S. Application Data

(60) Provisional application No. 61/608,697, filed on Mar. 9, 2012.

(51) Int. Cl.
*A61M 16/00* (2006.01)
*A61M 16/04* (2006.01)

(52) U.S. Cl.
CPC ....... *A61M 16/0497* (2013.01); *A61M 16/0465* (2013.01)

(58) Field of Classification Search
CPC ................. A61M 16/0465; A61M 16/0497; A61M 25/02; A61M 2025/026; A61M 2025/0266; A61M 2025/0273; A61M 16/04; A61M 16/0683; A61F 13/00
See application file for complete search history.

(56) References Cited

U.S. PATENT DOCUMENTS

| | | | | | |
|---|---|---|---|---|---|
| 2,765,792 | A | * | 10/1956 | Nichols | A61M 16/0472 128/200.26 |
| 2,923,299 | A | * | 2/1960 | Blackwood | A61M 16/0465 128/207.17 |
| 3,066,674 | A | * | 12/1962 | Capra | A61M 16/0468 128/207.16 |
| 3,225,767 | A | * | 12/1965 | Smith | A61M 16/0465 128/200.26 |
| 3,286,713 | A | * | 11/1966 | Kurtz | A61B 19/42 128/207.14 |
| 3,334,631 | A | * | 8/1967 | Stebleton | A61M 16/0465 128/200.26 |

(Continued)

OTHER PUBLICATIONS

Website printout; "Tracheotomy From Wikipedia, the fee encyclopedia," http://en.wikipedia.org/wiki/Tracheomony; printed Dec. 1, 2011; pp. 1-8.

(Continued)

*Primary Examiner* — Jason Flick
*Assistant Examiner* — Victoria Leszczak
(74) *Attorney, Agent, or Firm* — Calfee, Halter & Griswold LLP

(57) ABSTRACT

A collar for a tracheostomy tube, a method of securing a tracheostomy tube to the neck of a patient, and a medical device including a collar for the tracheostomy tube. In one exemplary embodiment, the collar includes a securing portion, a protection portion, and an attachment portion. The securing portion secures the tracheostomy tube to the neck of the patient. The protection portion extends from the securing portion and covers a portion of a flange of the tracheostomy tube. The protection portion is also positioned between the tracheostomy tube flange and the neck skin of the patient when the securing portion is attached to the tracheostomy tube. The attachment portion attaches the securing portion to the tracheostomy tube.

20 Claims, 6 Drawing Sheets

(56) References Cited

U.S. PATENT DOCUMENTS

| | | | | |
|---|---|---|---|---|
| 3,422,817 A * | 1/1969 | Mishkin | A61M 16/047 | 128/207.14 |
| 3,973,569 A * | 8/1976 | Sheridan | A61M 16/0465 | 128/207.15 |
| 4,331,144 A * | 5/1982 | Wapner | A61M 16/0488 | 128/207.17 |
| 4,340,046 A * | 7/1982 | Cox | A61M 16/04 | 128/200.26 |
| 4,649,913 A * | 3/1987 | Watson | A61M 16/0497 | 128/207.14 |
| 5,058,579 A * | 10/1991 | Terry | A61M 16/047 | 128/207.14 |
| 5,101,822 A * | 4/1992 | Kimmel | A61M 25/02 | 128/207.14 |
| 5,251,616 A * | 10/1993 | Desch | A61M 16/0465 | 128/200.26 |
| 5,443,064 A * | 8/1995 | Theis | A61M 16/0497 | 128/207.14 |
| 5,839,437 A * | 11/1998 | Briggs, III | A61M 16/0465 | 128/207.14 |
| 5,918,599 A * | 7/1999 | Shesol | A61M 16/0465 | 128/207.17 |
| 6,105,573 A * | 8/2000 | Delaplane | A61M 16/0488 | 128/200.26 |
| 6,105,577 A * | 8/2000 | Varner | A61M 16/0465 | 128/207.14 |
| 7,093,598 B1 * | 8/2006 | Hanneman | A61M 16/047 | 128/207.14 |
| 7,784,460 B2 * | 8/2010 | Djupesland | A61M 15/00 | 128/203.12 |
| 8,074,650 B2 * | 12/2011 | Steeves | A61M 16/047 | 128/200.24 |
| 8,096,300 B2 * | 1/2012 | Russo | A61M 16/0488 | 128/202.27 |
| 8,381,731 B2 * | 2/2013 | Jundt | A61M 16/0488 | 128/200.24 |
| 2007/0068531 A1 * | 3/2007 | Matlock | A61M 16/0465 | 128/207.15 |
| 2007/0144527 A1 * | 6/2007 | Wilson | A61M 16/0465 | 128/207.17 |
| 2009/0014010 A1 * | 1/2009 | Leckie | A61M 25/02 | 128/207.17 |
| 2009/0126740 A1 * | 5/2009 | Loescher | A61M 16/047 | 128/207.14 |
| 2010/0262093 A1 * | 10/2010 | Ballenger | A61M 16/047 | 604/304 |
| 2012/0073571 A1 * | 3/2012 | Djupesland | A61M 15/0091 | 128/200.23 |
| 2012/0222682 A1 * | 9/2012 | Nguyen | A61M 16/0497 | 128/207.17 |
| 2013/0174844 A1 * | 7/2013 | Doll | A61M 16/0497 | 128/204.18 |
| 2013/0213405 A1 * | 8/2013 | Dillworth | A61M 16/0497 | 128/207.17 |

OTHER PUBLICATIONS

Website printout; "Types of Tracheostomy Tubes," http://www.hopkinsmedicine.org/tracheostomy/about/types.html; printed Dec. 1, 2011; pp. 1-2.

* cited by examiner

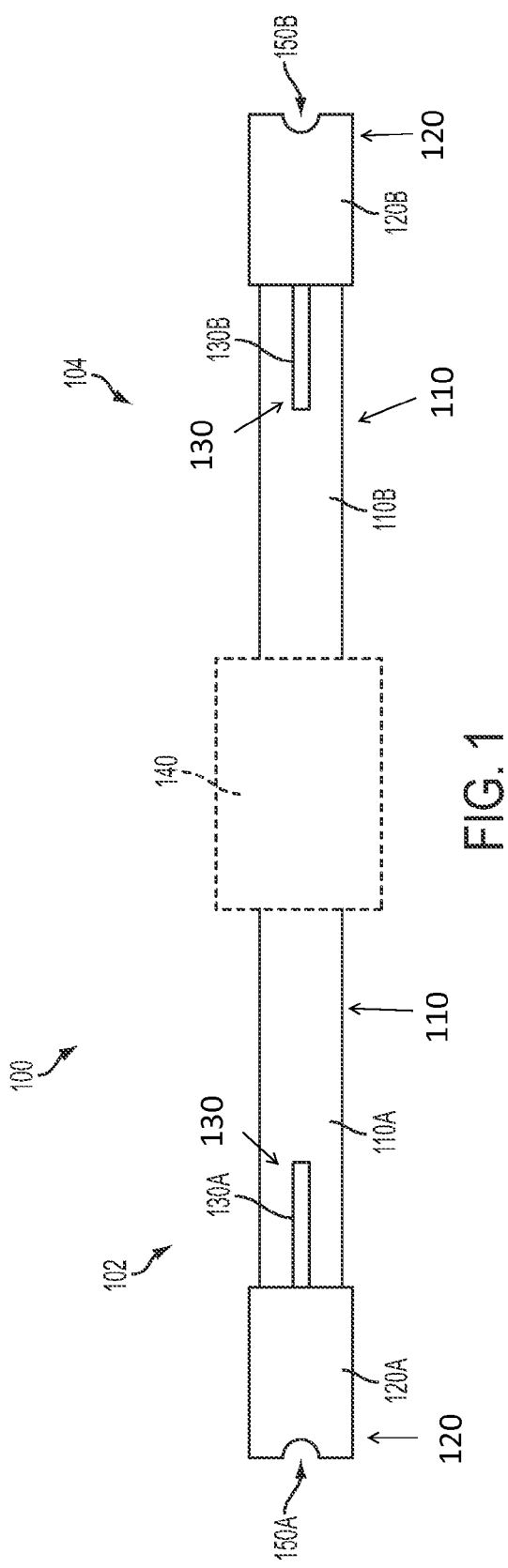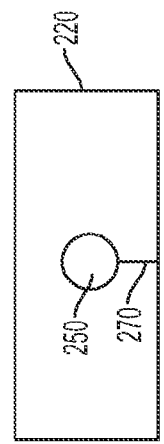

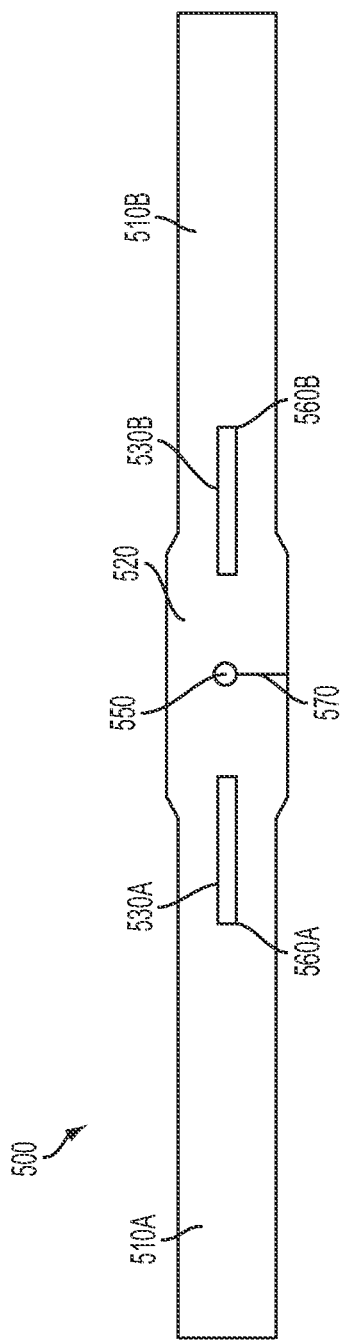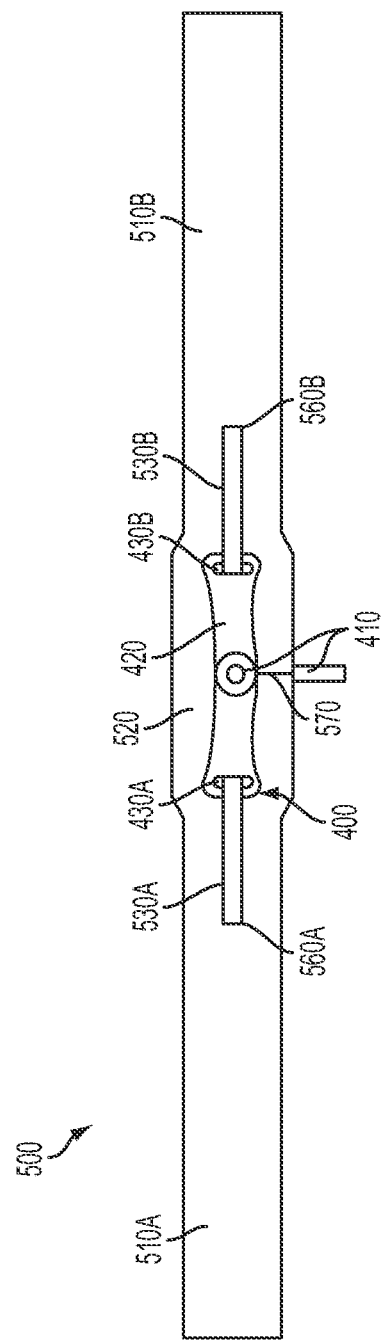

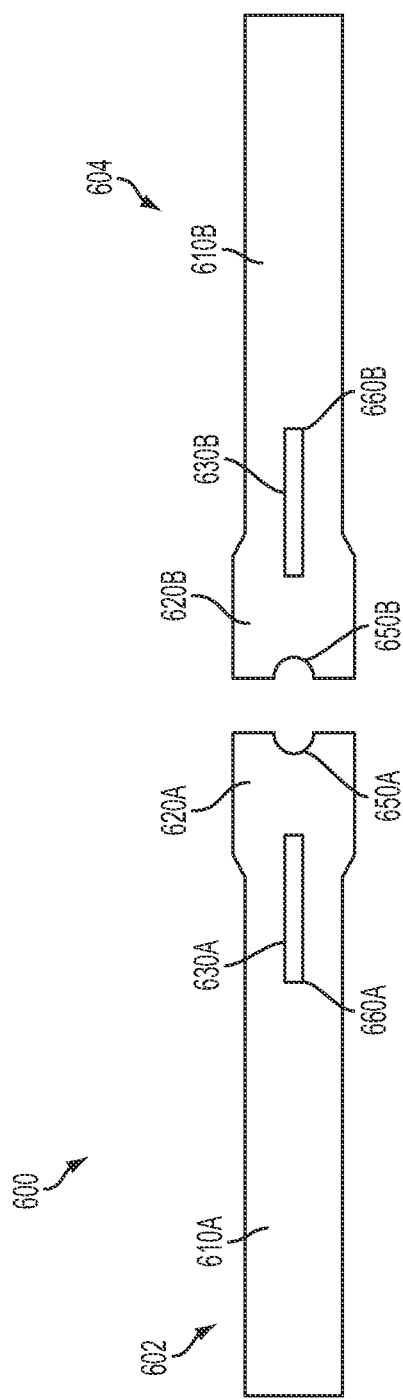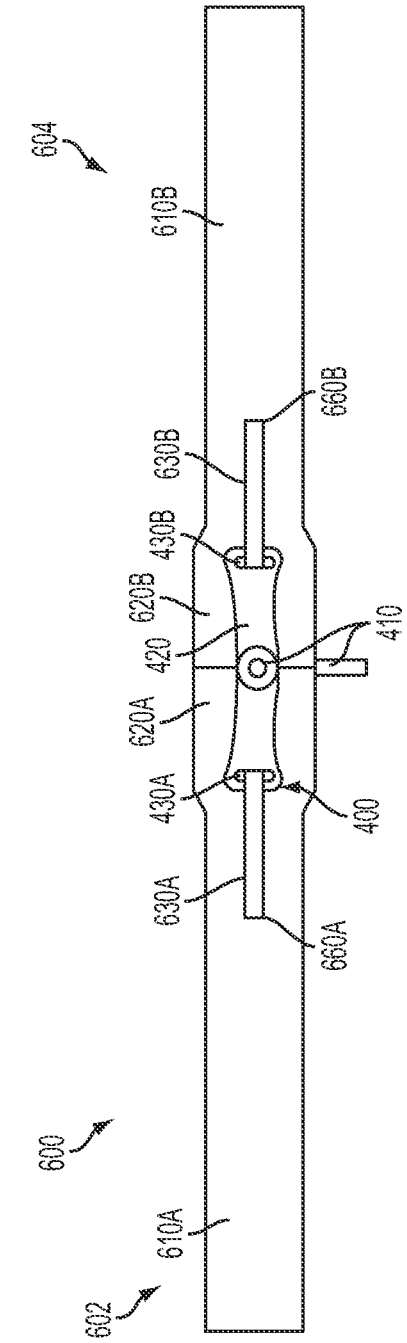

TRACHEOSTOMY TUBE COLLAR AND METHOD

CROSS REFERENCE TO RELATED APPLICATION

This application is a U.S. Non-Provisional Patent Application which claims priority to U.S. Provisional Patent Application No. 61/608,697 filed on Mar. 9, 2012 and titled "Tracheostomy Tube Collar and Method," which is hereby incorporated by reference in its entirety.

BACKGROUND

A tracheotomy is a surgical procedure that includes making an incision on the anterior aspect of the neck and opening an airway through an incision in the trachea. The resulting stoma can serve independently as an airway or as a site for a tracheostomy tube ("trach tube") to be inserted. The trach tube allows a patient to breathe without the use of his or her nose or mouth.

The trach tube generally consists of a curved tube that holds the stoma open. A flange or neck plate extends from the tube and has openings formed within it. Cloth ties or straps are generally attached to the openings in the flange of the trach tube and around the neck of the patient to hold the trach tube in place. The flange of the trach tube will often irritate and rub the skin on the anterior portion of the neck and the ties or straps will roll or slide causing the tie or strap to irritate the skin around the neck. As such, the ties or straps will often cause tissue breakdown, skin wounds, or irritation to the patient's neck.

SUMMARY

The present application discloses a collar for a trach tube, a method of securing a trach tube to the neck of a patient, and a medical device comprising a collar for the trach tube.

In one exemplary embodiment, the collar comprises a securing portion, a protection portion, and an attachment portion. The securing portion secures the trach tube to the neck of the patient. The protection portion extends from the securing portion and is sized and shaped to cover a portion of a flange of the trach tube. The protection portion is also positioned between the trach tube flange and the neck skin of the patient when the securing portion is attached to the trach tube. The attachment portion attaches the securing portion to the trach tube.

In another exemplary embodiment, the collar comprises a first and second securing portion, a first and second protection portion, and a first and second attachment portion. The first securing portion is removably and adjustably attached to the second securing portion to secure the trach tube to the neck of the patient. The first protection portion extends from the first securing portion and the second protection portion extends from the second securing portion. Each protection portion is sized and shaped to cover a portion of a flange of the trach tube. The first attachment portion attaches the first securing portion to the flange of the trach tube and the second attachment portion attaches the second securing portion to the flange of the trach tube. The first and second attachment portions may be removably attached to the flange of the trach tube and facilitate positioning and/or adjustment of the first and second protection portions relative to the flange. Movement of the first attachment portion relative to the flange of the trach tube positions the first protection portion between the flange and the neck skin of the patient and movement of the second attachment portion relative to the flange of the trach tube positions the second protection portion between the flange and the neck of the patient.

In one exemplary embodiment, the method of securing a trach tube to the neck of the patient comprises attaching an attachment portion of a collar to a flange of the trach tube. An attachment portion of the collar is moved relative to the flange of the trach tube to position a protection portion of the collar between the flange and the neck of the patient. The protection portion is sized and shaped to cover a portion of the flange. A securing portion of the collar is placed around the patient's neck to secure the trach tube to the neck of the patient.

BRIEF DESCRIPTION OF DRAWINGS

FIG. 1 illustrates a trach tube collar according to an embodiment of the present application.

FIG. 2 illustrates a protection portion of a trach tube collar according to an embodiment of the present application.

FIG. 5A illustrates a trach tube collar according to an embodiment of the present application.

FIG. 5B illustrates the trach tube collar of FIG. 5A attached to the exemplary trach tube of FIG. 4A.

FIG. 6A illustrates a trach tube collar according to an embodiment of the present application.

FIG. 6B illustrates the trach tube collar of FIG. 6A attached to the exemplary trach tube of FIG. 4A.

DESCRIPTION OF EMBODIMENTS

Figure 4A:
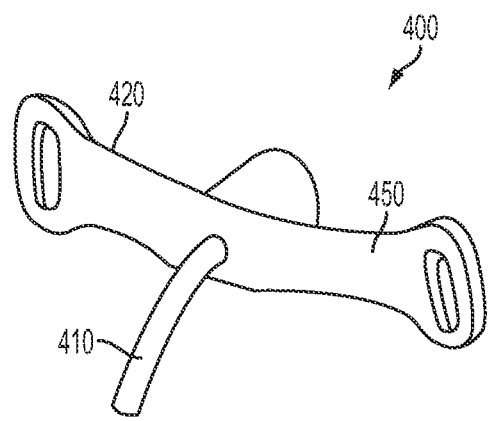
FIG. 4A is a rear perspective view of an exemplary trach tube.
Figure 4B:
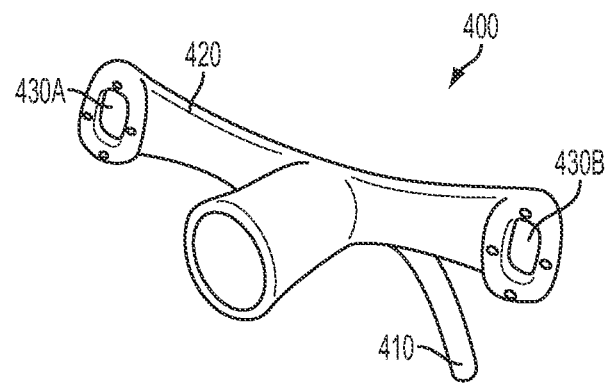
FIG. 4B is a front perspective view of the exemplary trach tube of FIG. 4A.

The present application discloses a trach tube collar for securing a trach tube to the neck of a patient. An exemplary trach tube 400 is illustrated in FIGS. 4A and 4B. The trach tube 400 includes a curved tube 410 and a flange or neck plate 420. The flange 420 includes openings or slots 430A, 430B and has a rear surface 450. The rear surface 450 of the trach tube 400 faces the neck of the patient when the trach tube is inserted into stoma. As illustrated in FIGS. 4A and 4B, the trach tube 400 is a pediatric trach tube. In certain embodiments, the curved tube 410 of the trach tube 400 has an inner diameter of 3.0 mm, an outer diameter of 4.3 mm, and a length of 36 mm. However, the trach tube collar of the present application may be used with a variety of trach tubes, including neonatal, pediatric, and/or adult sized trach tubes.

The trach tube collar of the present application is configured to prohibit the flange or neck plate of the trach tube from directly irritating or rubbing the patient's skin. The collar may also be configured such that it does not roll or slide, thus, also prohibiting the collar from irritating the skin around the patient's neck.

The trach tube collar of the present application is also adjustable. For example, the collar may be adjusted for use with a variety of patient neck sizes. The collar is also adjustable such that it may be used with a variety of trach tubes, such as trach tubes of various shapes and sizes. For example, the collar may be used with neonatal, pediatric, and/or adult sized trach tubes.

To prohibit the flange of the trach tube from directly irritating or rubbing the skin on the patient's neck, medical professionals will sometimes lodge gauze material or the like between the flange of the trach tube and the skin. To accomplish this, the medical professionals may need to cut pieces of the gauze material to place between the flange and the skin. However, the gauze material can move and become dislodged. The gauze material is also in close proximity to the stoma (an open wound) and may contact the wound or be pushed into the wound. Furthermore, some gauze material may become saturated with fluid and become wet, which increases the risk of infection. The trach tube collar of the present application generally comprises one or more pieces of material that are automatically positioned between the flange of the trach tube and the skin of the patient's neck when the collar is attached to the trach tube. The one or more pieces of material prohibit the flange of the trach tube from directly irritating or rubbing the patient's skin. The collar also holds the one or more pieces of material, or the protective portion, in place without the use of an adhesive. Furthermore, the one or more pieces of material may be adjusted relative to the trach tube to accommodate trach tubes of various types, shapes, and sizes.

FIG. 1 illustrates a trach tube collar 100 according to an embodiment of the present application. As shown, the collar 100 comprises a first part 102 and a second part 104. The first part 102 is removably and adjustably attached to the second part 104 to form the collar 100. The first part 102 and the second part 104 of the collar 100 each comprise a securing portion 110, a protection portion 120, and an attachment portion 130. The securing portions 110 secure the trach tube to the patient's neck. The protection portions 120A and 120B prohibit the flange of the trach tube from directly irritating or rubbing the patient's neck. The attachment portions 130 removably attach the collar 100 to the flange of the trach tube. The first part 102 and/or the second part 104 of the collar 100 may be made from a unitary piece of material or a plurality of components attached or otherwise secured together.

The first part 102 of the collar 100 is attached to the second part 104 by an adjustment feature 140. The adjustment feature 140 permits the length or circumference of the collar 100 around the neck of the patient to be adjusted by moving the first part 102 relative to the second part 104. As such, the collar 100 may be adjusted to fit around a variety of patient neck sizes. Adjusting the length of the collar 100 around the neck of the patient may be accomplished in a variety of ways. For example, the adjustment feature 140 may be a buckle, clasp, spaced protrusions/openings, slide, Velcro®, or other adjustment mechanisms or fasteners that facilitate adjustment of the first part 102 relative to the second part 104 and attach the first part to the second part.

As illustrated in FIG. 1, a first securing portion 110A of the first part 102 is removably and adjustably attached to a second securing portion 110B of the second part 104 by the adjustment feature 140. Each securing portion 110A, 110B is generally made from a unitary piece of material. A variety of fabric or strap materials may be used for the securing portions, such as, for example, neoprene, Gortex®, nylon, polyester, polypropylene, cotton, spandex, or elastane. However, a variety of other fabric or strap materials may be used.

The securing portions of the collar may or may not include a variety of other properties or features. For example, one or more of the securing portions may be elastic, rubberized, or may include one or more pieces of Velcro®. The securing portions may also comprise a moisture-wicking fabric. The securing portions may also be water resistant such that they do not absorb bodily fluids. The securing portions may also comprise an antimicrobial material or a material with antimicrobial properties. Further, the securing portions may be coated with an antimicrobial material or have one or more antimicrobial materials embedded in the securing portion.

Figure 3:
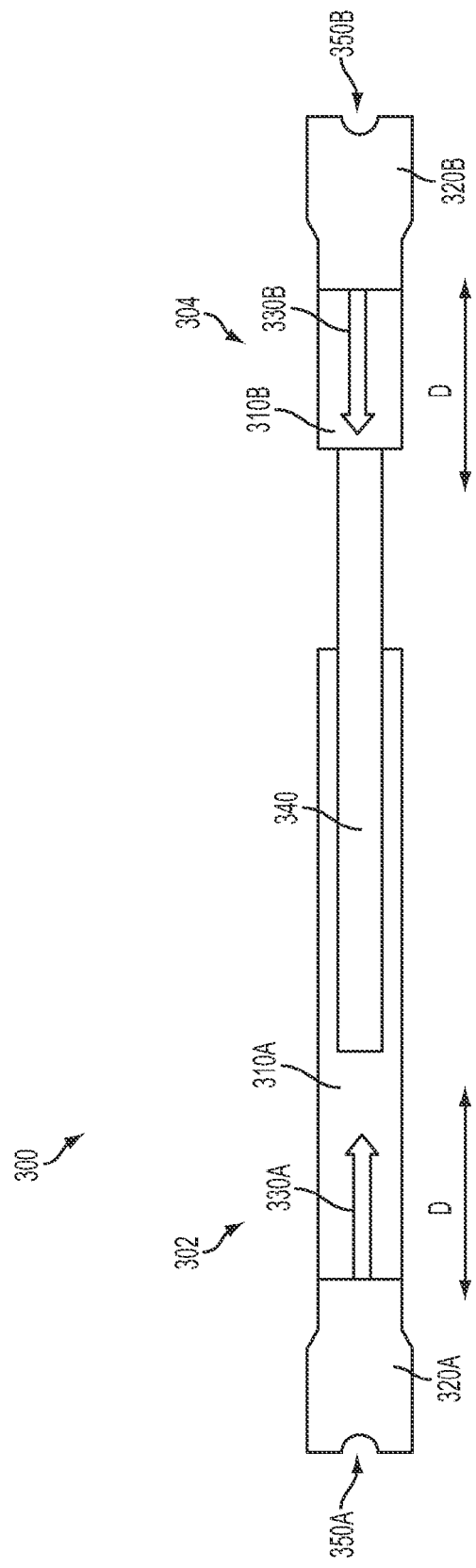
FIG. 3 illustrates a trach tube collar according to an embodiment of the present application.

FIG. 3 illustrates a trach tube collar 300 according to another embodiment of the present application. As shown in FIG. 3, a first part 302 of the collar 300 is removably and adjustably attached to a second part 304 with Velcro® to form the collar 300. The second part 304 includes a strap 340 extending from a second securing portion 310B of the second part 304. The strap 340 comprises a hook fabric that attaches to loop fabric on a first securing portion 310A of the first part 302. As such, the strap 340 of the second part 304 may be attached to the first securing portion 310A at any of an infinite number of locations to fit a variety of patient neck sizes. In other embodiments, the fabrics of the strap 340 and the first securing portion 310A may be reversed. For example, the strap 340 may comprise a loop fabric and the first securing portion 310A may comprise a hook fabric.

The securing portion of the collar may include features that prohibit the securing portion from directly irritating or rubbing the neck of the patient. For example, the securing portions 110, 310 of the collars 100, 300 may be wider than conventional ties or straps such that the force applied to the neck of the patient by the collar 100, 300 is spread over a larger surface area than conventional ties or straps. For example, in some embodiments, the securing portions 110, 310 may be between about ½ and 1½ inches wide. Furthermore, wider securing portions prohibit rolling or creasing of the collar when tensioned around the neck of the patient. The securing portions 110, 310 may also include a friction enhancing surface, such as a rubber backing, textured material, or the like, that prohibits the securing portion from sliding on the neck of the patient. The surfaces of the securing portions 110, 310 contacting the patient's neck may also include an adhesive that holds the collar 100, 300 in place relative to the neck of the patient. In one embodiment, the securing portions of the collar are about ⅞ inch wide and have a rubber backing on the inner surface contacting the patient's neck.

The protection portion of the collar may extend from the securing portion or the attachment portion of the collar. As illustrated in FIG. 1, the protection portion 120 of the collar 100 extends from the securing portion 110. A first protection portion 120A extends from the first securing portion 110A and a second protection portion 120B extends from the second securing portion 110B. The protection portions 120A, 120B are sized and shaped to fit between the trach tube flange and the anterior aspect of the patient's neck. As such, the protection portions 120A, 120B prohibit the flange of the trach tube from rubbing or otherwise directly irritating the patient's skin.

Similarly, as illustrated in FIG. 3, a first protection portion 320A extends from the first securing portion 310A and a second protection portion 320B extends from the second securing portion 310B. The protection portions 320A, 320B are sized and shaped to fit between the trach tube flange and the anterior aspect of the patient's neck. As such, the protection portions 320A, 320B prohibit the flange of the trach tube from rubbing or otherwise irritating the patient's skin.

The protection portions of the collar are generally made from a unitary piece of padded material that prohibits the flange of the trach tube from rubbing or otherwise irritating the patient's skin. The protection portions may comprise a variety of padding materials, such as, for example, neoprene, Gortex®, nylon, polyester, polypropylene, cotton, spandex or elastane. However, a variety of other padding materials may be used.

The protection portions of the collar may or may not include a variety of other properties or features. For example, one or more of the protection portions may be capable of being wiped dry of bodily fluids and/or comprise a facing or finish on one or more surfaces that permits the protection portion to be wiped dry of bodily fluids. The protection portions may also comprise a moisture-wicking fabric. The protection portions may be water resistant such that they do not absorb bodily fluids. The protection portions may also comprise an antimicrobial material or a material with antimicrobial properties. Further, the protection portions may be coated with an antimicrobial material or have one or more antimicrobial materials embedded in the protection portion. The protection portions may also be elastic, rubberized, or may include one or more pieces of Velcro®.

The protection portion of the collar is sized and shaped to cover a portion of the rear surface of the trach tube flange. In some embodiments, the protection portions 120A, 120B, 320A, and 320B of the collars 100, 300 may be between about 1 and 2½ inches long and between about ½ and 1½ inches wide. However, these ranges are only exemplary and the protection portions 120A, 120B, 320A, and 320B can be any size to fit the trach tube flange. The protection portions 120A, 120B, 320A, and 320B may also be sized so that the trach tube is not significantly moved when the protection portions are inserted between the flange and the patient's neck. For example, in some embodiments, the protection portions 120A, 120B, 320A, and 320B may be between about 0.01 and 0.25 inch thick. In one embodiment, each protection portion of the collar comprises a unitary piece of material about 1¾ inches long, about 1¼ inches wide, and about 1/16 inch thick.

Each protection portion may be sized and shaped to cover a portion of the rear surface of the trach tube. As illustrated in FIGS. 1 and 3, each protection portion 120A, 120B, 320A, and 320B of the collars 100, 300 is sized and shaped to substantially cover about one half of the rear surface of the trach tube flange. The first protection portion 120A, 320A of the collars 100, 300 has a cutout or notch 150A, 350A sized and shaped to at least partially surround a first half of the tube of the trach tube. Similarly, the second protection portion 120B, 320B has a cutout or notch 150B, 350B sized and shaped to at least partially surround a second half of the tube of the trach tube. Thus, when the collar 100, 300 is attached to the flange of the trach tube, the protection portions 120A and 120B, 320A and 320B of each collar 100, 300 collectively substantially cover the entire rear surface of the flange and provide an opening for the tube of the trach tube. The collars 100, 300 prohibit the rear surface of the trach tube flange from rubbing or otherwise directly irritating the patient's skin.

The protection portion(s) of the present application may be configured to cover various amounts of the rear surface of the trach tube flange. For example, in certain embodiments, the protection portion(s) is sized and shaped to cover greater than half of the rear surface of the flange, or between about 51% and about 100% of the rear surface of the trach tube flange. In certain embodiments, the protection portion(s) is sized and shaped to cover about 55%, about 75%, about 80%, about 95%, or about 100% of the rear surface of the trach tube flange. Further, the protection portion(s) may be configured to cover substantially all or the entire rear surface of the trach tube flange. Further, the protection portion(s) moves the rear surface of the trach tube flange away from the skin to prohibit the trach tube flange from irritating the skin.

The attachment portion of the collar is generally attached to either the securing portion or the protection portion of the collar. For example, as illustrated in FIG. 1, a first attachment portion 130A extends from an end of the first securing portion 110A and a second attachment portion 130B extends from an end of the second securing portion 110B. The attachment portions 130A and 130B attach the collar 100 to the flange of the trach tube. Furthermore, the attachment portions 130A and 130B are removable from the flange of the trach tube such that the collar 100 may be attached to, detached from, or reattached to the flange of the trach tube. The attachment portions 130A and 130B may also be used to adjust the position of the protection portions 120A and 120B between the flange and the neck of the patient. The attachment portions 130A and 130B may be a variety of features that facilitate adjustment of the protection portions 120A and 120B and attachment of the collar 100 to the flange of the trach tube. For example, the attachment portions 130A and 130B may include a buckle, clasp, spaced protrusions/openings, slide, a Velcro® strap, or other adjustment mechanisms or fasteners.

The attachment portions 130A and 130B may also comprise straps and/or ties sized and shaped to fit through the openings in the flange of the trach tube. The straps and/or ties are generally made from a unitary piece of material. The material of the straps and/or ties may be a variety of fabric or strap materials, such as, for example, neoprene, Gortex®, nylon, polyester, polypropylene, cotton, spandex or elastane. However, a variety of other fabric or strap materials may be used.

The attachment portions of the collar may or may not include a variety of other properties or features. For example, the attachment portions may be elastic, rubberized, or may include one or more pieces of Velcro®. The attachment portions may also comprise a moisture-wicking fabric. The attachment portions may also be water resistant such that they do not absorb bodily fluids. The attachment portions may also comprise an antimicrobial material or a material with antimicrobial properties. Further, the attachment portions may be coated with an antimicrobial material or have one or more antimicrobial materials embedded in the attachment portion.

In certain embodiments, the attachment portions are extensions of the securing portion of the collar such that the attachment portions and the securing portion are a unitary component of the collar. For example, the attachment portions may be an end of the securing portion that is attached to the flange of the trach tube. The collar may comprise one or more securing portions for securing the trach tube to the neck of the patient. Furthermore, one or more protection portions may extend from the attachment portion or the securing portion of the collar.

As illustrated in FIG. 3, the collar 300 comprises a first attachment portion 330A extending from an end of the first securing portion 310A and a second attachment portion 330B extending from an end of the second securing portion 310B. The attachment portions 330A, 330B are straps having a hook fabric on one surface. The straps are sized and shaped to fit through the openings in the flange of the trach tube. Furthermore, the straps comprise a pointed end that facilitates feeding the end of the strap through the opening in the flange.

The collar 300 is attached to the trach tube by feeding the straps of the attachment portions 330A, 330B through the openings in the flange from the rear of the trach tube between the flange and the neck of the patient. As the straps are pulled through the openings, the protection portions 320A, 320B are automatically positioned between the flange of the trach tube and the neck of the patient. Furthermore, as illustrated in FIG. 3, pulling the end of the straps of the attachment portions 330A, 330B in a direction D moves the protection portions 320A, 320B towards and away from the trach tube. For example, pulling the end of the straps in the direction D and away from the trach tube moves the corresponding protection portion closer to the trach tube and vice versa. As such, the straps of the attachment portions 330A, 330B may be used to adjust the position of the protection portions 320A, 320B between the flange of the trach tube and the patient's neck. The protection portions 320A, 320B each have an edge that at least partially surrounds a tube of the trach tube when the pieces of protection material 320A, 320B are positioned between the flange and the neck skin of the patient. Securing the collar 300 to the patient and adjusting the attachment portions 330A, 330B causes the edges of the protection portions 320A, 320B to move towards each other.

Once the protection portions 320A, 320B are positioned relative to the trach tube, the straps of the attachment portions 330A, 330B may then be secured to the securing portions 310A, 310B or flange of the trach tube to hold the protection portions in position relative to the trach tube. For example, the strap of the attachment portions 320A, 320B may include one or more pieces of Velcro® that attaches to the securing portion 310A, 310B. However, other methods of securing the strap of the attachment portions 330A, 330B may be used, such as clips, ties, snaps, pins, buckles, clasps, spaced protrusions/openings, slides, or other fasteners.

The protection portions 320A, 320B are held in place between the flange of the trach tube and the neck of the patient by the attachment portions 330A, 330B at a first end and the cutout or notch 350A, 350B at least partially surrounding the tube at a second end. Furthermore, when the collar 300 is secured around the neck of the patient, the flange of the trach tube presses against the protection portions 320A, 320B to hold the protection portions in place against the neck of the patient. The protection portions of the collar may also include a friction enhancing surface, such as a rubber backing, textured surface, or the like, that prohibits the protection portion from moving between the flange of the trach tube and the neck of the patient. The protection portions of the collar may also be configured to attach to the trach tube flange, such as with one or more pieces of Velcro®, to hold the protection portion in place relative to the flange.

Once the collar is attached to the trach tube, the collar is then secured around the neck of the patient. For example, in regards to collars 100, 300 and as described above, the first part 102, 302 of the collar is attached to the second part 104, 304 to secure the collar around the neck of the patient. Furthermore, the first part 102, 302 and the second part 104, 304 permit the collar 100, 300 to be secured around the neck of the patient without application of an uneven force on the flange of the trach tube that may substantially move the trach tube and/or damage the stoma. For example, once the trach tube is inserted into the stoma, each part of the collar 100, 300 may be attached to the flange of the trach tube. The first part 102, 302 and the second part 104, 304 of the collar 100, 300 may then be attached together at a location on the rear or side of the neck and adjusted about the neck. During adjustment of the collar 100, 300, substantially even tension may be applied to each side of the flange by using the first part 102, 302 and the second part 104, 304. As such, the collar 100, 300 may be secured to the neck of the patient without applying uneven force on the trach tube that may substantially move the trach tube and/or damage the stoma.

FIGS. 6A and 6B illustrate a trach tube collar 600 according to an embodiment of the present application. Both FIGS. 6A and 6B illustrate the front side of the collar 600 facing away from the neck of the patient and the rear side of the collar is against the skin of the patient to provide protection. The collar 600 comprises a first part 602 and a second part 604. As shown, the first part 602 and the second part 604 are made from a unitary piece of material. The first part 602 is removably and adjustably attached to the second part 604 to form the collar 600. The first part 602 and the second part 604 of the collar 600 each comprise a securing portion 610, a protection portion 620, and an attachment portion 630. The securing portions 610 secure the trach tube to the patient's neck. The collar 600 may comprise an adjustment feature that adjusts the length or circumference of the securing portions 610 around the neck of the patient. The protection portions 620 prohibit the flange of the trach tube from irritating or rubbing the patient's neck. The attachment portions 630 removably attach the collar 600 to the flange of the trach tube.

Figure 7:
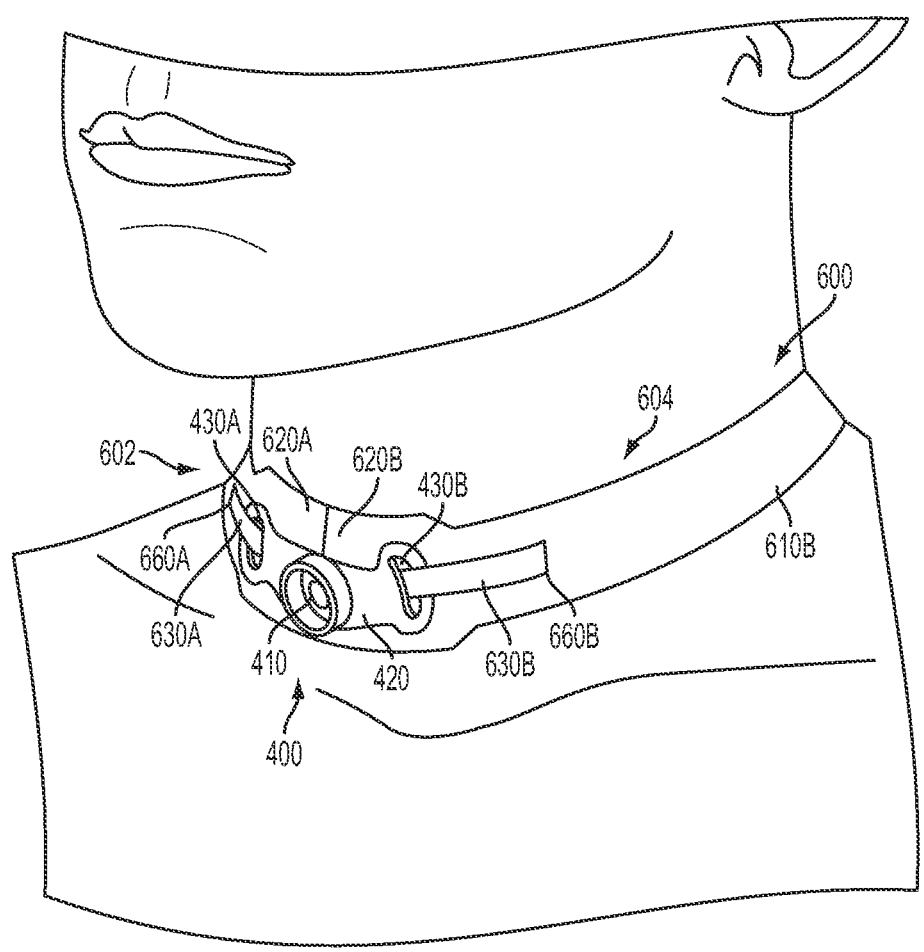
FIG. 7 illustrates the trach tube collar of FIG. 6A and the exemplary trach tube of FIG. 4A secured to the neck of a patient.

FIG. 6B illustrates the collar 600 attached to the exemplary trach tube 400 without the first part 602 and the second part 604 of the collar attached together around the patient's neck. FIG. 7 illustrates the collar 600 and the exemplary trach tube 400 secured to the neck of a patient. As illustrated in FIGS. 6B and 7, when the collar 600 is attached to the trach tube 400, the protection portions 620A, 620B collectively substantially cover the entire rear surface 450 of the flange 420 of the trach tube and provide an opening for the tube 410. As such, the collar 600 prohibits the rear surface 450 of the flange 420 from rubbing or otherwise irritating the patient's skin.

As illustrated in FIGS. 6B and 7, the ends 660A, 660B of the attachment portions 630A, 630B are fed through the openings 430A, 430B in the flange 420 of the trach tube 400 from the rear of the trach tube. As the attachment portions 630A, 630B are pulled through the openings 430A, 430B, the protection portions 620A, 620B are automatically positioned between the flange 420 and the neck of the patient. Furthermore, pulling the attachment portions 630A, 630B towards and away from the trach tube 400 moves the protection portions 620A, 620B towards and away from the trach tube.

Once the protection portions 620A, 620B are positioned relative to the trach tube 400, the attachment portions 630A, 630B may then be secured to the securing portions 610A, 610B. For example, the attachment portions 630A, 630B may comprise a hook fabric that attaches to the loop fabric on the securing portion 610A, 610B to secure the attachment portion to the securing portion. As shown in FIGS. 6B and 7, the protection portions 620A, 620B are held in place between the flange 420 of the trach tube 400 and the neck of the patient by the attachment portions 630A, 630B at a first end and the cutout or notch 650A, 650B at least partially surrounding the tube 410 at a second end.

Furthermore, when the first part 602 and the second part 604 of the collar 600 are attached to secure the collar around the neck of the patient, the first part and the second part apply tension on each side of the flange 420 of the trach tube 400. As such, the collar 600 may be secured to the neck of the patient without applying uneven force on the trach tube 400 that may substantially move the trach tube and/or damage the stoma.

In some embodiments, the trach tube collar of the present application comprises a single protection portion extending from one or more securing portions. For example, FIG. 2 illustrates a single protection portion 220 sized and shaped to fit between the entire trach tube flange and the patient's neck and has an opening 250 for the tube of the trach tube. A slit 270 extends from the opening 250 to an upper or lower edge of the protection portion 220 such that the protection portion may be placed between the flange and the patient's neck and around the tube of the trach tube.

The single protection portion of the present application may be configured to cover various amounts of the rear surface of the trach tube flange. For example, in certain embodiments, the protection portion is sized and shaped to cover greater than half of the rear surface of the flange, or between about 51% and about 100% of the rear surface of the trach tube flange. In certain embodiments, the protection portion is sized and shaped to cover about 55%, about 75%, about 80%, about 95%, or about 100% of the rear surface of the trach tube flange. Further, the protection portion may be configured to cover substantially all or the entire rear surface of the trach tube flange. Further, the protection portion moves the rear surface of the trach tube flange away from the skin to prohibit the trach tube flange from irritating the skin.

FIGS. 5A and 5B illustrate a trach tube collar 500 according to an embodiment of the present application. Both FIGS. 5A and 5B illustrate the front side of the collar 500 facing away from the neck of the patient and the rear side of the collar is against the skin of the patient to provide protection. As shown, the collar 500 is a single part comprising a first securing portion 510A, second securing portion 510B, single protection portion 520, first attachment portion 530A, and second attachment portion 530B. The first securing portion 510A may be adjustably and removably attached to the second securing portion 510B to secure the trach tube to the patient's neck. The collar 500 may comprise an adjustment feature that adjusts the length or circumference of the securing portions 510A, 510B around the neck of the patient. The protection portion 520 prohibits the flange of the trach tube from irritating or rubbing the patient's neck. The attachment portions 530 removably attach the collar 500 to the flange of the trach tube.

FIG. 5B illustrates the collar 500 attached to an exemplary trach tube 400 without the first securing portion 510A and the second securing portion 510B of the collar attached together around the patient's neck. As shown, when the collar 500 is attached to the trach tube 400, the protection portion 520 substantially covers the entire rear surface 450 of the flange 420 of the trach tube and provide an opening for the tube 410. As such, the collar 500 prohibits the rear surface 450 of the flange 420 from rubbing or otherwise irritating the patient's skin.

As shown in FIGS. 5A and 5B, a slit 570 extends from an opening 550 in the protection portion 520 to a lower edge such that the protection portion may be placed between the flange 420 of the trach tube 400 and the patient's neck and around the tube 410. The ends 560A, 560B of the attachment portions 530A, 530B are then fed through the openings 430A, 430B in the flange 420 of the trach tube 400 from the rear of the trach tube. Once the protection portion 520 is positioned relative to the trach tube 400, the attachment portions 530A, 530B may then be secured to the securing portions 510A, 510B. For example, the attachment portions 530A, 530B may comprise a hook fabric that attaches to the loop fabric on the securing portion 510A, 510B to secure the attachment portion to the securing portion. As shown in FIG. 5B, the protection portion 520 is held in place between the flange 420 of the trach tube 400 and the neck of the patient by the attachment portions 530A, 530B and the opening 550 surrounding the tube 410.

In some embodiments, the collar 500 may be tightened or adjusted about the neck of the patient by decreasing the length of the single part around the neck of the patient. The collar 500 may be tightened and/or adjusted from the rear or sides of the neck such that substantially even tension is applied on each side of the flange 420 of the trach tube 400 to secure the collar about the neck of the patient. Furthermore, if needed, the single part collar 500 may be easily altered to form a two part collar by cutting the protection portion 520 between the opening 550 and the upper edge of the protection portion.

One or more protections portion of the trach tube collar of the present application may include an opening or slit in the bottom portion of the protection portion such that the stoma is visible to medical personnel when the trach tube is secured to the patient's neck. Furthermore, the material of the protection portion of the trach tube collar of the present application may be easily cut such that it may be quickly removed by medical personnel.

As described herein, when one or more components are described as being connected, joined, affixed, coupled, attached, or otherwise interconnected, such interconnection may be direct as between the components or may be in direct such as through the use of one or more intermediary components. Also as described herein, reference to a "member," "component," or "portion" shall not be limited to a single structural member, component, or element but can include an assembly of components, members or elements.

While the present invention has been illustrated by the description of embodiments thereof, and while the embodiments have been described in considerable detail, it is not the intention of the applicants to restrict or in any way limit the scope of the invention to such details. Additional advantages and modifications will readily appear to those skilled in the art. For example, where components are releasably or removably connected or attached together, any type of releasable connection may be suitable including for example, locking connections, fastened connections, tongue and groove connections, etc. Still further, component geometries, shapes, and dimensions can be modified without changing the overall role or function of the components. Therefore, the inventive concept, in its broader aspects, is not limited to the specific details, the representative apparatus, and illustrative examples shown and described. Accordingly, departures may be made from such details without departing from the spirit or scope of the applicant's general inventive concept.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

We claim:

1. A collar for a tracheostomy tube, comprising:
a securing portion for securing the tracheostomy tube to a patient;
a protection portion extending from the securing portion, wherein the protection portion covers a portion of a flange of the tracheostomy tube, and wherein the protection portion is configured to be positioned between the tracheostomy tube flange and the neck skin of the patient and pressed against the neck skin by the tracheostomy tube flange to hold the protection portion in place and prohibit the flange from rubbing the neck skin of the patient, and wherein the protection portion is formed from first and second pieces of protection material separately extending from the securing portion; and
an attachment portion for attaching the securing portion to the tracheostomy tube, wherein the attachment portion comprises first and second pieces of attachment material capable of independently adjusting the first and second pieces of protection material, respectively, relative to the tracheostomy tube flange to position the pieces of protection material between the flange and the neck skin of the patient;
wherein the first and second pieces of protection material each have an edge that at least partially surrounds a tube of the tracheostomy tube when the pieces of protection material are positioned between the flange and the neck skin of the patient;
wherein upon securing the collar to the patient and adjusting the first and second pieces of attachment material causes the edges of the first and second pieces of protection material to move towards each other.

2. The collar of claim 1 further comprising an adjustment feature for adjusting the securing portion around the neck of the patient.

3. The collar of claim 1, wherein the protection portion substantially covers a rear surface of the tracheostomy tube flange when the securing portion is attached to the tracheostomy tube, and wherein the protection portion prohibits the tracheostomy tube flange from directly rubbing the skin on the patient's neck.

4. The collar of claim 1, wherein the first and second pieces of protection material portion are sized and shaped to collectively substantially cover a rear surface of the tracheostomy tube flange.

5. The collar of claim 1, wherein the first and second pieces of protection material are automatically positioned between tracheostomy tube flange and the patient's neck when the securing portion is attached to the tracheostomy tube.

6. The collar of claim 1, wherein the securing portion comprises a first securing portion removably and adjustably attached to a second securing portion for securing the tracheostomy tube to the neck of the patient, and wherein the first piece of protection material extends from the first securing portion and the second piece of protection material extends from the second securing portion.

7. The collar of claim 6, wherein the first piece of attachment material attaches the first securing portion to the flange of the tracheostomy tube and the second piece of attachment material attaches the second securing portion to the flange of the tracheostomy tube.

8. The collar of claim 7, wherein movement of the first attachment material relative to the flange of the tracheostomy tube positions the first protection material between the flange and the neck of the patient and movement of the second attachment material relative to the flange of the tracheostomy tube positions the second protection material between the flange and the neck of the patient.

9. The collar of claim 1, wherein the protection portion comprises an antimicrobial padding material that prohibits the flange of the tracheostomy tube from rubbing the neck skin of the patient.

10. The collar of claim 1, wherein the attachment portion comprises a strap having a pointed end to facilitate insertion of the strap into an opening in the flange of the tracheostomy tube.

11. The collar of claim 1, wherein at least one of the first and second pieces of protection material comprises a notch that at least partially surrounds the tube of the tracheostomy tube.

12. A collar for a tracheostomy tube, comprising:
a first securing portion removably and adjustably attached to a second securing portion for securing the tracheostomy tube to the neck of a patient;
a first protection portion extending from the first securing portion and a second protection portion extending from the second securing portion, wherein each protection portion is sized and shaped to cover a portion of a flange of the tracheostomy tube; and
a first attachment portion for attaching the first securing portion to the flange of the tracheostomy tube and a second attachment portion for attaching the second securing portion to the flange of the tracheostomy tube;
wherein movement of the first attachment portion relative to the flange of the tracheostomy tube positions the first protection portion between the flange and the neck of the patient and movement of the second attachment portion relative to the flange of the tracheostomy tube positions the second protection portion between the flange and the neck of the patient; and
wherein the first and second protection portions are configured to be pressed against the neck skin by the tracheostomy tube flange to hold the protection portion in place and prohibit the flange from rubbing the neck skin of the patient;
wherein the first and second protection portions each have an edge that at least partially surrounds a tube of the tracheostomy tube when the protection portions are positioned between the flange and the neck skin of the patient;
wherein upon securing the collar to the patient and adjusting the first and second pieces of attachment material causes the edges of the first and second pieces of protection material to move towards each other.

13. A method of securing a tracheostomy tube to the neck of a patient, comprising the steps of:
attaching an attachment portion of a collar to a flange of the tracheostomy tube;
moving the attachment portion of the collar to position a protection portion of the collar between the flange and the neck skin of the patient, wherein the protection portion covers a portion of the flange and is formed from first and second pieces of protection material, and wherein the attachment portion comprises first and second pieces of attachment material capable of independently adjusting the first and second pieces of protection material, respectively, relative to the tracheostomy tube flange to position the pieces of protection material between the flange and the neck skin of the patient, and wherein the first and second pieces of protection material each have an edge that at least partially surrounds a tube of the tracheostomy tube when the pieces of protection material are positioned between the flange and the neck skin of the patient;

placing a securing portion of the collar around the patient's neck to secure the tracheostomy tube to the patient;

securing the attachment portion such that the protection portion is pressed against the neck skin by the tracheostomy tube flange to hold the protection portion in place and prohibit the flange from rubbing the neck skin of the patient; and adjusting the first and second pieces of attachment material causing the edges of the first and second pieces of protection material to move towards each other.

14. The method of claim 13 further comprising adjusting the securing portion to fit around the patient's neck.

15. The collar of claim 1, wherein the first and second pieces of protection material are separately attached to the securing portion.

16. The collar of claim 6, wherein the first piece of protection material attaches to the first securing portion and the second piece of protection material attaches to the second securing portion.

17. The collar of claim 12, wherein the first and second protection portions are attached to the first and second securing portions, respectively.

18. The method of claim 13, wherein the first and second pieces of protection material extend from the securing portion.

19. The method of claim 18, wherein the first and second pieces of protection material are separately attached to the securing portion.

20. The method of claim 13, wherein the securing portion comprises a first securing portion attached to a second securing portion for securing the tracheostomy tube to the neck of the patient, and wherein the first piece of protection material extends from the first securing portion and the second piece of protection material extends from the second securing portion.

* * * * *